United States Patent [19]

Pommer et al.

[11] 4,001,416

[45] Jan. 4, 1977

[54] CERTAIN FUNGICIDAL PYRIDINES

[75] Inventors: Ernst-Heinrich Pommer, Limburgerhof; Bernd Zeeh, Ludwigshafen; Norbert Goetz, Bobenheim-Roxheim; Bjoern Giergensohn, Ludwigshafen, all of Germany

[73] Assignee: BASF Aktiengesellschaft, Ludwigshafen (Rhine), Germany

[22] Filed: Mar. 19, 1975

[21] Appl. No.: 559,686

[30] Foreign Application Priority Data

Apr. 9, 1974 Germany ........................... 2417216

[52] U.S. Cl. ........................... 424/266; 424/DIG. 8; 424/251

[51] Int. Cl.² .......................................... A01N 9/22

[58] Field of Search ..................... 424/DIG. 8, 266; 260/295.5

[56] References Cited

UNITED STATES PATENTS

| 3,711,486 | 1/1973 | Torba | 424/266 |
|---|---|---|---|
| 3,822,277 | 7/1974 | Dufour | 424/266 |

*Primary Examiner*—V. D. Turner
*Attorney, Agent, or Firm*—Johnston, Keil, Thompson & Shurtleff

[57] ABSTRACT

New and valuable fungicides containing pyridinecarboxylic acid derivatives and a process for controlling fungi with these compounds.

9 Claims, No Drawings

CERTAIN FUNGICIDAL PYRIDINES

The present application relates to new and valuable fungicides containing pyridinecarboxylic acid derivatives and a process for controlling fungi with these compounds.

It is known that caboxylic anilides have an action on fungi, especially those of the Basidiomycetes class. For instance, German Laid-Open Application DOS No. 1,642,224 discloses the use of o-chlorobenzoic anilide as a fungicide. However, its action is unsatisfactory.

We have now found that compounds of the formula

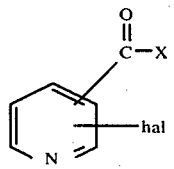

where the two radicals hal and

have to be in ortho-position to each other and hal denotes chloro, bromo or iodo and X denotes $NH-R^1$, $R^1$ denoting cycloalkyl of 5 or 6 carbon atoms, cyclohexyl substituted hydroxy, methyl, ethyl, isopropyl or by ethynyl, $R^1$ further denoting naphthyl, indanyl, pyridyl or pyrimidyl which may be substituted by methyl, amino and/or hydroxy, or the radical

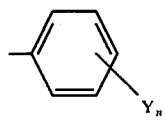

$n$ denoting one of the integers 1, 2, 3 and 4 and Y denoting hydrogen, $C_1$ to $C_4$ alkyl, fluoro, chloro, bromo, iodo, hydroxy, amino, phenyl, $C_1$ to $C_3$ alkoxy, acetyl, benzoyl, trifluoromethyl, phenoxy, chlorophenoxy, hydroxycarbonyl, $C_1$ to $C_4$ alkoxycarbonyl, hydroxycarbonylmethyl or nitro, or X denotes

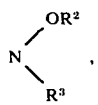

$R^2$ denoting hydrogen or methyl and $R^3$ denoting cyclohexyl, have a good action on injurious fungi, especially of the Basidiomycetes class, e.g., Rhizoctonia, Coniophora and Tilletia, and of the Ascomycetes class, e.g., Erysiphe. The agents according to the invention may also be used in salt form with acids, e.g., as hydrochlorides, or with bases.

The fungicidal agents are of special interest for combatting fungus diseases in various crops, e.g.

| | |
|---|---|
| Ustilago scitaminea | (sugarcane smut) |
| Hemileia vastatrix | (coffee disease) |
| Uromyces fabae (or appendiculatus) | (bean rust) |
| Puccinia recondita | (leaf rust of wheat) |
| Puccinia coronata | (crown rust of oats) |
| Puccinia striiformis | (yellow rust) |
| Puccinia hordei | (barley rust) |
| Erysiphe graminis v. hordei | (barley mildew) |
| Rhizoctonia solani in cotton and soybeans. | |

By crop plants we mean in this connection in particular wheat, rye, barley, oats, rice, Indian corn, cotton, soybeans, broadbeans, coffee, sugarcane and garden ornamentals.

The agents are systemic. This systemic action is of particular importance in connection with the control of internal plant diseases such as rust in cereals.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coaltar oils, etc., and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc., are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of sulfonated naphthalene and naphthalene derivatives with formaldehyde, condensation products of naphthalene naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contains from 0.1 to 95, and preferably 0.5 to 90% by weight of active ingredient.

Depending on the type of effect to be achieved, the application rates are from 0.2 to 5 and more, preferably 0.5 to 2, kg/ha of active ingredient. The active ingredients may also be mixed with other prior art fungicides. In many cases the spectrum of fungicidal action is increased. A member of these fungicidal compositions also demonstrate synergism, i.e., the fungicidal action of the composition is greater than that of the individual components when added together.

The following active ingredients have proved to be particularly suitable for combinations:
dithiocarbamates and derivatives thereof, e.g.,
ferric dimethyldithiocarbamate (ferbam)
zinc dimethyldithiocarbamate (ziram)
manganese ethylenebisdithiocarbamate (maneb)
zinc ethylenebisdithiocarbamate (zineb)
tetramethylthiuram disulfide (thiram)
manganese-zinc ethylenediamine-bisdithiocarbamate
zinc-(N,N'-propylene-1,2-bisdithiocarbamate)
ammonia complex of zinc-(N,N'-ethylene-bisdithiocarbamate) and
N,N'-polypropylene-bis-(thiocarbamoyl)-disulfide
ammonia complex of zinc-(N,N'-propylene-bisdithiocarbamate) and
N,N'-polypropylene-bis-(thiocarbamoyl)-disulfide
3,5-dimethyl-1,3,5-2H-tetrahydrothiadiazine-2-thione
nitrophenol derivatives, such as
dinitro-(1-methylheptyl)-phenylcrotonate (dinocap)
2-sec-butyl-4,6-dinitrophenyl-3,5-dimethylacrylate (binapacryl)
2-sec-butyl-4,6-dinitrophenylisopropylcarbonate
heterocyclic structures, such as
N-trichloromethylthiotetrahydrophthalimide (captan)
N-trichloromethylthiophthalimide (folpet)
N-(1,1,2,2-tetrachloroethylthio)-tetrahydrophthalimide
N,N-dimethyl-N-phenyl-(N-fluorodichloromethylthio)-sulfamide
N-methyl-N-phenyl-(N'-fluorodichloromethylthio)-N'-methylsulfamide
2-heptadecyl-2-imidazoline (glyodin)
2,4-dichloro-6-(o-chloroanilino)-s-triazine
diethylphthalimidophosphorothioate
5-amino-1-[bis-(dimethylamino)-phosphynyl]-3-phenyl-1,2,4-triazole
5-ethoxy-3-trichloromethyl-1,2,4-thiadiazole
2,3-dicyano-1,4-dithiaanthraquinone (dithianon)
2-thio-1,3-dithio-[4,5-b]-quinoxaline (thioquinox)
methyl 1-(butylcarbamoyl)-2-benzimidazolecarbamate
2-methoxycarbonylaminobenzimidazole
methyl 1-(5-cyanopentylcarbamoyl)-2-benzimidazolecarbamate
2-thiocyanomethylthiobenzothiazole (busan)
4-(2-chlorophenylhydrazono)-3-methyl-5-isooxazolone
pyridine-2-thiol-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
5,5-dimethyl-3-(3,5-dichlorophenyl)-2,4-dioxo-1,3-oxazolidine
2-[furyl-(2)]-benzimidazole
piperazine-1,4-diyl-bis[1-(2,2,2-trichloroethyl)-formamide]
2-[thiazolyl-(4)]-benzimidazole
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene (thiophanat)
1,2-bis-(3-methoxycarbonyl)-2-thioureido)-benzene
and various fungicides, such as
dodecylguanidine acetate (dodine)
3-[2-(3,5-dimethyl-2-oxycyclohexyl)-2-hydroxyethyl]-glutarimide(cycloheximide)
hexachlorobenzene
2,6-dimethyl-N-tridecylmorpholine and its salts
2,6-dimethyl-N-cyclododecylmorpholine and its salts
2,3-dichloro-1,4-naphthoquinone
1,4-dichloro-2,5-dimethoxybenzene
p-dimethylaminobenzenediazosodium sulfonate
2-chloro-1-nitropropane
polychloronitrobenzenes, such as pentachloronitrobenzene, methyl isothiocyanate, fungicidal antibiotics such as griseofulvin and kasugamycin, tetrafluorodichloroacetone, 1-phenylthio semicarbazide, Bordeaux mixture, nickel-containing compounds and sulfur.

These agents may be added to the fungicides of the invention in a weight ratio of from 1:10 to 10:1. If desired, they may also be added immediately before use (tankmix).

The active ingredients may be prepared by known processes, as illustrated by the following examples.

EXAMPLE 1

27.7 parts (by weight) of 2-bromonicotinic acid and 10.1 parts of triethylamine in 200 parts of methylene chloride are placed in a vessel. At −20° C, 11.9 parts of thionyl chloride in 30 parts of methylene chloride is dripped in, after which the temperature of the mixture is allowed to rise to room temperature. After the mixture has been stirred for 3 hours at this temperature, 9.3 parts of aniline and 10.1 parts of triethylamine are dripped in. The mixture is allowed to after-react for 1 hour at 35° C. After extraction with water, the organic phase is separated, dried and concentrated. After crystallization from benzene there is obtained 25.3 parts of 2-bromonicotinic anilide, m.p.: 168° to 170° C.

EXAMPLE 2

12.6 parts of N-cyclohexylhydroxylamine and 14 parts of sodium carbonate in 125 parts of dioxane and 30 parts of water are placed in a reactor. At 0° to 5° C and over a period of 15 minutes, 17.6 parts of 2-chloronicotinyl chloride in 30 parts of dioxane is dripped into the reaction solution, which is then allowed to after-react for 1 hour. The solution is concentrated and the residue taken up in chloroform, followed by extraction with water, drying and concentration. Crystallization from a mixture of benzene and ligroin yields 15 parts of 2-chloronicotinic acid-N-hydroxy-N-cyclohexylamide, m.p.: 151° to 153° C.

EXAMPLE 3

20 parts of potassium carbonate in 25 parts of water is added to a solution of 16.9 parts of 2-chloronicotinic acid-N-hydroxy-N-cyclohexylamide in 50 parts of dioxane. At 45° C, 12.6 parts of dimethyl sulfate is dripped into the reaction solution and the whole stirred for 30 minutes at 45° C. The reaction product is precipitated by the addition of water. Crystallization from a mixture of benzene and ligroin yields 14.8 parts of 2-chloronicotinic acid-N-cyclohexyl-N-methoxyamide, m.p.: 96° to 98° C.

EXAMPLE 4

13.5 parts of 4-chloronicotinic acid and 9.6 parts of triethylamine are dissolved in 200 parts of methylene chloride, and the solution is cooled to −10° C. At this temperature, 11.3 parts of thionyl chloride is added. The mixture is stirred for 1 hour at −5° to −10° C.

This solution is added, with ice cooling, to 8 parts of aniline and 8.7 parts of triethylamine. The mixture is stirred for 1 hour at 40° C and then cooled. The precipitated hydrochloride is suction filtered and the filtrate concentrated.

The crystal slurry is extracted several times with benzene. After removal of the benzene, there is obtained 16.2 parts of 4-chloronicotinic anilide. It is not possible to determine exactly the melting point as decomposition occurs.

NMR spectrum (in DDMSO at 100 $MH_z$ and TMS as internal reference): $\delta$ = 8.76 ppam (singlet), $\delta$ = 8.62 (doublet), $\delta$ = 7.68 (multiplet), $\delta$ = 7.70 (doublet), $\delta$ = 7.37 (triplet), $\delta$ = 7.10 (triplet), $\delta$ = 10.60 (singlet, broad).

EXAMPLE 5

11.9 parts of thionyl chloride is dripped into a solution of 24.9 parts of 3-iodoisonicotinic acid (m.p. 246° to 247° C, prepared by oxidation of 3-iodo-4-methylpyridine with potassium permanganate) in 150 parts of benzene. The mixture is subsequently stirred at 40° to 45° C until hydrogen chloride ceases to evolve. At 40° C, 10.1 parts of triethylamine and 9.3 parts of aniline are then added and the whole is allowed to after-react for 1 hour. The product is worked up as in Example 1. After crystallization from benzene there is obtained 20 parts of 3-iodoisonicotinic anilide, m.p.: 160° to 162° C.

Examples of other compounds which may be prepared in accordance with the above examples are as follows:

|  | m.p. (° C) |
|---|---|
| 2-chloronicotinic anilide | 122–124 |
| hydrochloride of 2-chloronicotinic anilide | 132–133 |
| 2-chloronicotinic acid-2'-methylanilide | 166–170 |
| 2-chloronicotinic acid-3'-methylanilide | 147–148 |
| 2-chloronicotinic acid-4'-methylanilide | 183–184 |
| 2-chloronicotinic acid-2'-ethylanilide | 139–140 |
| 2-chloronicotinic acid-2',3'-dimethylanilide | 185–186 |
| 2-chloronicotinic acid-2',4'-dimethylanilide | 168–169 |
| 2-chloronicotinic acid-2',5'-dimethylanilide | 208–209 |
| 2-chloronicotinic acid-2',6'-dimethylanilide | 141–142 |
| 2-chloronicotinic acid-2'-phenylanilide | 119–120 |
| 2-chloronicotinic acid-3',4'-dimethylanilide | 148–149 |
| 2-chloronicotinic acid-3',5'-dimethylanilide | 174–175 |
| 2-chloronicotinic acid-3',5'-diethylanilide | 153–154 |
| 2-chloronicotinic acid-4'-isopropylanilide | 138–139 |
| 2-chloronicotinic acid-2',4',6'-trimethylanilide | 164–165 |
| 2-chloronicotinic acid-2',4',5'-trimethylanilide | 210–211 |
| 2-chloronicotinic acid-4'-phenylanilide | 198–199 |
| 2-chloronicotinic acid-2'-chloroanilide | 120–121 |
| 2-chloronicotinic acid-3'-chloroanilide | 125–126 |
| 2-chloronicotinic acid-4'-chloroanilide | 148–149 |
| 2-chloronicotinic acid-3',4'-dichloroanilide | 185–186 |
| 2-chloronicotinic acid-4'-iodoanilide | 175–177 |
| 2-chloronicotinic acid-2'-hydroxyanilide | 155–156 |
| 2-chloronicotinic acid-3',4'-difluoroanilide | 119–120 |
| 2-chloronicotinic acid-3'-hydroxyanilide | 177–178 |
| 2-chloronicotinic acid-2'-methyl-3'-chloroanilide | 183–184 |
| 2-chloronicotinic acid-3'-ethylanilide | 130–131 |
| 2-chloronicotinic acid-4'-ethylanilide | 146–147 |
| 2-chloronicotinic acid-3'-methoxy-4'-methylanilide | 143–144 |
| 2-chloronicotinic acid-2',5'-dimethoxyanilide | 124–125 |
| 2-chloronicotinic acid-2',5'-dimethoxy-4'-chloroanilide | 138–139 |
| 2-chloronicotinic acid-3',5'-dichloro-4'-methoxyanilide | 154–156 |
| 2-chloronicotinic acid-3'-trifluoromethylanilide | 107–109 |
| 2-chloronicotinic acid-1'-naphthylamide | 170–172 |
| 2-chloronicotinic acid-2'-aminoanilide | 176–178 |
| 2-chloronicotinic cyclohexylamide | 129–135 |
| 2-chloronicotinic acid-2'-hydroxycyclohexylamide | 192–194 |
| 2-chloronicotinic acid-1'-ethynylcyclohexylamide | 139–141 |
| 2-chloronicotinic cyclopentylamide | 113–115 |
| 2-chloronicotinic acid-2'-methylcyclohexylamide | 160–163 |
| 2-chloronicotinic acid-3'-methylcyclohexylamide | 145–147 |
| 2-chloronicotinic acid-4'-methylcyclohexylamide | 108–110 |
| 2-chloronicotinic acid-4'-isopropylcyclohexylamide | 154–155 |
| 2-chloronicotinic acid-4'-hydroxycyclohexylamide | 200–202 |
| 2-chloronicotinic acid-3'-aminoanilide | 202 |
| 2-chloronicotinic acid-4'-aminoanilide | 154–157 |
| 2-chloronicotinic acid-3',5'-(bis-n-butoxycarbonyl)-anilide | 98–100 |
| 2-chloronicotinic acid-3'-nitroanilide | 157–158 |

-continued

| | m.p. (° C) |
|---|---|
| 2-chloronicotinic acid-5'-indanylamide | 150–152 |
| 2-chloronicotinic acid-N-(2'-pyridyl)-amide | 130 |
| 2-chloronicotinic acid-N-(3'-pyridyl)-amide | 158–160 |
| 2-chloronicotinic acid-N-(4'-pyridyl)-amide monohydrate | 96–98 |
| 2-chloronicotinic acid-N-2'-(4',6'-dimethylpyrimidyl)-amide | 160–161 |
| 2-chloronicotinic acid-N-4'-(2',6'-dimethylpyrimidyl)-amide | 176–177 |
| 2-chloronicotinic acid-N-2'-(4'-hydroxy-6'-methyl-pyrimidyl)-amide | 280 (decomposes) |
| 2-chloronicotinic acid-N-2'-(6'-aminopyridyl)-amide | 157–159 |
| 2-bromonicotinic cyclohexylamide | 143–145 |
| 3-iodopicolinic anilide | 97–99 |
| 3-iodoisonicotinic cyclohexylamide | 178–180 |
| 3-chloropicolinic anilide | 78 |
| 2-chloronicotinic acid-2'-methoxycarbonylthioureido-anilide | 197–198 |
| 2-chloronicotinic acid-2'-ethoxycarbonylthioureido-anilide | 160–163 |
| 2-chloronicotinic acid-4'-(p-chlorophenoxy)-anilide | 154–156 |
| 2-chloronicotinic acid-4'-benzoylanilide | 114–115 |
| 2-chloronicotinic acid-2'-fluoroanilide | oily |
| 2-chloronicotinic acid-3'-fluoroanilide | 102–103 |
| 2-chloronicotinic acid-4'-fluoroanilide | 93–94 |
| 2-chloronicotinic acid-2'-isopropylanilide | 138–139 |
| 2-chloronicotinic acid-2',6'-diisopropylanilide | 203–204 |
| 2-chloronicotinic acid-2'-hydroxycarbonylanilide | 232–233 |
| 2-chloronicotinic acid-3'-hydroxycarbonylanilide | 208 |
| 2-chloronicotinic acid-4'-hydroxycarbonylanilide | 217 |
| hydrochloride of 4-chloronicotinic anilide | |
| hydrochloride of 4-chloronicotinic cyclohexylamide | |

The following examples describe the biological action of the agents according to the invention on various crop plants suffering from fungus diseases.

EXAMPLE 6

Leaves of barley seedlings grown in pots are sprayed with aqueous emulsions consisting to the extent of 80% of active ingredient and 20% of emulsifier. After the layer has dried, the leaves are dusted with spores of barley mildew (*Erysiphe graminis var. hordei*). The plants are then placed in a greenhouse at a temperature of 20° to 22° C and having a relative humidity of 75 to 80%. After 10 days the extent of fungus spread is assessed.

0 = no attack, graduated down to
5 = leaves completely covered with fungus

| Active ingredient | Leaf attack after spraying with x% active ingredient liquor | |
|---|---|---|
| | 0.25% | 0.12% |
| [2-hydroxynicotinic acid cyclohexylamide structure with OH, CO-NH, N, Cl] | 0 | 1 |
| [2-methoxynicotinic acid cyclohexylamide structure with OCH₃, CO-NH, N, Cl] | 1 | 2 |
| [o-toluanilide structure with CH₃, CO-NH] (German Laid-Open Application DOS 1,642,224) | 4 | 5 |
| Control (untreated) | | 5 |

EXAMPLE 7

Leaves of oat plants grown in pots are artificially infected with spores of crown rust (*Puccinia coronata*), and the plants placed in a steam-saturated chamber for 48 hours at 20° to 25° C. The plants are then sprayed with aqueous liquors which contain, dissolved in water or emulsified, a mixture of 80% of the active ingredient under examination and 20% of sodium lignin sulfonate. The plants are then placed in a greenhouse at a temperature of 20° to 22° C and having a relative humidity of 75 to 80%. After 10 days the extent of fungus spread is assessed.

| Active ingredient | Leaf attack after spraying with x% active ingredient liquor | |
|---|---|---|
| | 0.2% | 0.1% |
| 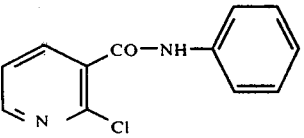 | 0 | 0 |
| 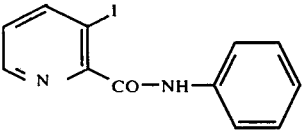 | 0 | 1 |
| 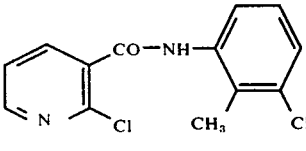 | 0 | 1 |
| 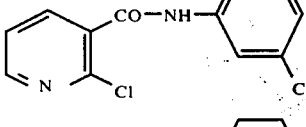 | 0 | 1 |
| 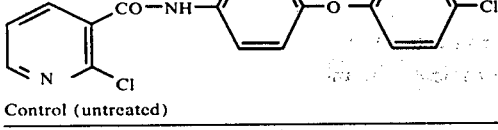 | 0 | 0 |
| Control (untreated) | | 5 |

EXAMPLE 8

Leaves of bean plants grown in pots are artificially infected with spores of bean rust (*Uromyces fabae*) and the plants are then placed in a steam-saturated chamber for 48 hours at 20° to 25° C. The plants are then sprayed with aqueous liquors which contain, dissolved in water or emulsified, a mixture of 80% of the active ingredient under examination and 20% of sodium lignin sulfonate. The plants are then placed in a greenhouse at a temperature of 20° to 22° C and having a relative humidity of 75 to 80%. After 10 days the extent of fungus spread is assessed.

| Active ingredient | Leaf attack after spraying with x% active ingredient liquor | |
|---|---|---|
| | 0.2% | 0.1% |
| 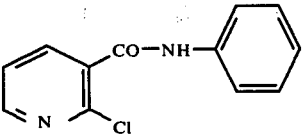 | 0 | 0 |
| 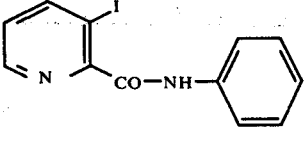 | 0 | 1 |
| 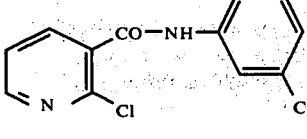 | 0 | 1 |

-continued

| Active ingredient | Leaf attack after spraying with x% active ingredient liquor | |
|---|---|---|
| | 0.2% | 0.1% |
| 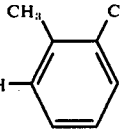 | 0 | 1 |
| 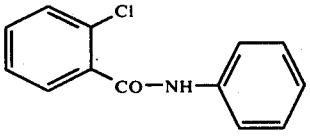 (German Laid-Open Application DOS 1,642,224) | 1 | 2 |
| Control (untreated) | 5 | |

EXAMPLE 9

The fungicidal action of the active ingredients under investigation on *Rhizoctonia solani* is examined in a soil treatment experiment employing cotton of the "Delta Pine" variety. The active ingredients, in amounts of 0.02, 0.01 and 0.005%, with reference to the weight of the soil, are carefully mixed with compost which has been artificially inoculated with the fungus *Rhizoctonia solani*. Wooden boxes 60×40×6 cm are filled with this soil (depth: 5 cm) and 100 cotton seeds of the "Delta Pine" variety are then sown into this soil at a distance apart of 3 to 5 cm and a depth of 3 cm. The boxes are placed in a greenhouse at a temperature of 22° to 25° C. After 21 days the number of healthy cotton plants is counted.

| Active ingredient | Percentage of healthy plants after 21 days in infected compost Active ingredient concentrations | | |
|---|---|---|---|
| | 0.02 | 0.01 | 0.005 |
| 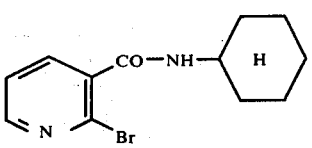 | 86 | 75 | 65 |
| 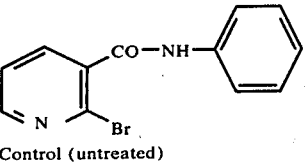 | 100 | 83 | 74 |
| Control (untreated) | 12 | | |

We claim:

1. A process for combatting fungi which comprises treating the fungi or the crop plants to be protected against fungal attack with a fungicidal amount of a pyridine compound of the formula

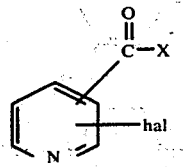

the two radicals hal and

being in ortho-position to each other, wherein hal denotes chloro, bromo or iodo and X denotes NH—$R^1$, $R^1$ being a member selected from the group consisting of: cycloalkyl of 5 or 6 carbon atoms; cyclohexyl substituted by hydroxy, methyl, ethyl, isopropyl or ethynyl; phenyl; naphthyl; indanyl; pyridyl; pyridyl substituted by amino; pyrimidyl substituted by methyl or hydroxy; and the radical

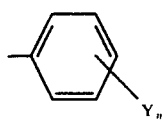

in which n is one of the integers, 1, 2, 3 and 4 and Y is hydrogen, $C_1$ to $C_4$ alkyl, fluoro, chloro, bromo, iodo, hydroxy, amino, phenyl, $C_1$ to $C_3$ alkoxy, acetyl, benzoyl, trifluoromethyl, phenoxy, chlorophenoxy, hydroxycarbonyl, $C_1$ to $C_4$ alkoxycarbonyl, hydroxycarbonylmethyl or nitro;

or X denotes

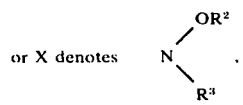

$R^2$ being hydrogen or methyl and $R^3$ being cyclohexyl.

2. A process as claimed in claim 1 wherein the pyridine compound as the active ingredient is applied to the crop plants to be protected at an application rate of about 0.2 to 5 kilograms per hectare.

3. A process as claimed in claim 1 wherein the fungi being treated are a member selected from the group consisting of the Basidiomycetes class and the Ascomycetes class.

4. A process as claimed in claim 1 wherein said pyridine compound has the formula

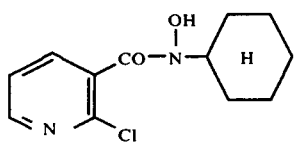

5. A process as claimed in claim 1 wherein said pyridine compound has the formula

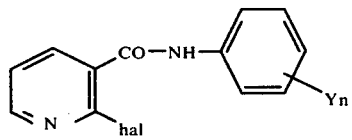

6. A process as claimed in claim 1 wherein said pyridine compound has the formula

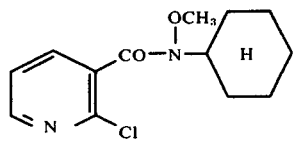

in which hal and Yn have the same meanings as given in claim 1.

7. A process as claimed in claim 1 wherein said pyridine compound has the formula

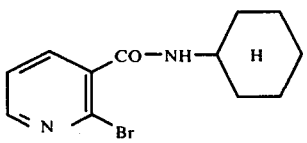

8. A process as claimed in claim 1 wherein said pyridine compound has the formula

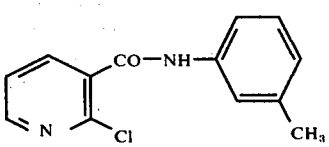

9. A process as claimed in claim 1 wherein said pyridine compound has the formula

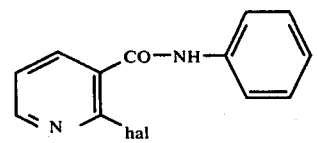

in which hal is chloro, bromo or iodo.

* * * * *